(12) United States Patent
Metzner (10) Patent No.: US 7,553,834 B2
(45) Date of Patent: Jun. 30, 2009

(54) METHOD FOR THE TARGETED TREATMENT OF DEPRESSION

(76) Inventor: Richard J. Metzner, 916 N. Foothill Rd., Beverly Hills, CA (US) 90210

( * ) Notice: Subject to any disclaimer, the term of this patent is extended or adjusted under 35 U.S.C. 154(b) by 1204 days.

(21) Appl. No.: 10/199,529

(22) Filed: Jul. 19, 2002

(65) Prior Publication Data
US 2004/0015055 A1 Jan. 22, 2004

(51) Int. Cl.
  A61K 31/34 (2006.01)
  A61K 31/135 (2006.01)
  A61K 31/15 (2006.01)
  A61K 31/36 (2006.01)
  A61K 31/045 (2006.01)
  A61K 31/55 (2006.01)
  G01N 33/48 (2006.01)
  G01N 33/50 (2006.01)
  G06F 19/00 (2006.01)
  G06G 7/48 (2006.01)
  G06G 7/58 (2006.01)

(52) U.S. Cl. .................. 514/212.05; 514/464; 514/469; 514/640; 514/646; 514/649; 514/730; 702/19; 703/11

(58) Field of Classification Search .................. 434/236; 514/469, 646, 640, 464, 649, 730, 212.05; 702/19; 703/11
See application file for complete search history.

(56) References Cited

U.S. PATENT DOCUMENTS 5,882,203 A * 3/1999 Correa et al. ............... 434/236

OTHER PUBLICATIONS

Metzner R. "TTDI System Background". [Online], 2007 [Retrieved on Sep. 5, 2007]. Retrieved from the Internet: <URL:http://ttdi.info. TTDISite/id1.html>.*
Metzner R. "An Introduction to the TTDI". [Online], 2007 [Retrieved on Sep. 5, 2007]. Retrieved from the Internet: <URL:http://www.ttdi. info>.*
Metzner R. "TTDI Questionnaire". [Online], 2007 [Retrieved on Sep. 5, 2007]. Retrieved from the Internet: <URL:http://www.ttdi. info>.*
Metzner R. "Using the TTDI System". [Online], 2008 [Retrieved on Sep. 5, 2007]. Retrieved from the Interent: <URL:http://www.ttdi. info>.*
Dalery, J. et al., "Agitated-anxious versus blunted-retarded major depressions: different clinical effects of fluoxetine," L'Encephale, 1995, 217-225, vol. XXI.
Filteau, M.J. et al., "SSRIs in anxious-agitated depression: a post-hoc analysis of 279 patients," International Clinical Psychopharmacology, 1995, 51-54, vol. 10.
Clerc, G.E., et al. "A double-blind comparison of venlafaxine and fluoxetine in patients hospitalized for major depression and melancholia," International Clinical Psychopharmacology, 1994, 139-143, vol. 9.

Davidson, J.R.T. et al., "The eight-item treatment-outcome post-traumatic stress disorder scale: a brief measure to assess treatment outcome in post-traumatic stress disorder," International Clinical Psychopharmacology, 1997, 41-45,vol. 12.
Heninger, G.R., et al., "The Revised Monoamine Theory of Depression: A Modulatory Role for Monoamines, Based on New Findings from Monoamine Depletion Experiments in Humans," Pharmacopsychiat, 1996, 2-11, vol. 29.
Opbroek, A, et al., "Emotional blunting associated with SSRI-induced sexual dysfunction. Do SSRIs inhibit emotional responses?," International Journal of Neuropsychopharmacology, 2002, 147-151, vol. 5, CINP, Cleveland, Ohio.
Zung, William W.K., "A Self-Rating Depression Scale," Archives of General Psychiatry, Jan. 1965, 63-70, vol. 12.
Hamilton, Max, "A Rating Scale for Depression," J. Neurol. Neurosurg. Psychiat., 1960, 56-62, vol. 23.
Beck, A.T. et al., "An Inventory for Measuring Depression," Archives of General Psychiatry, Jun. 1961, 53-63, vol. 4.
Swartz, Conrad M., et al., "Melancholia with Onset During Treatment with SSRIs", Annals of Clinical Psychiatry, Nov. 4, 1998, 177-179, vol. 10.
Rampello, L., et al. "Comparative Effects of Amitriptyline and Amineptine in Patients Affected by Anxious Depression," Neuropsychobiology, 1995, 130-134, vol. 31.
Andiné, P., et al., "Successful use of a selective serotonin reuptake inhibitor in a patient with multiple chemical sensitivities" 1997, 82-83, vol. 96, Acta Psychiatrica Scandinavica.
Barr, Linda C. et al., "Addition of Desipramine to Serotonin Reuptake Inhibitors in Treatment-Resistant Obsessive-Compulsive Disorder," American Journal of Psychiatry, Sep. 1997, 1293-1295, vol. 154:9.
Pearlstein, Teri B. et al., "Comparison of Fluoxetine, Bupropion, and Placebo in the Treatment of Premenstrual Dysphoric Disorder," Journal of Clinical Psychopharmacology, 1997, 261-266, vol. 17, No. 4.
Stahl, Stephen, "Mixed Depression and Anxiety: Serotonin $_{1A}$ Receptors as a Common Pharmacologic Link," J Clinical Psychiatry, 1997, 20-26, vol. 58 (suppl 8).
Andrews, William et al., "The SSRI antidepressants: Exploring their "other" possible properties" Journal of Affective Disorders, 1998, 141-144, vol. 49, Elsevier Science B.V.
Kaye, Walter et al., "Serotonin Neuronal Function and Selective Serotonin Reuptake Inhibitor Treatment in Anorexia and Bulimia Nervosa" Society of Biological Psychiatry, 1998, 825-838, vol. 44.
Kyle, C.J. et al., "Comparison of the Tolerability and Efficacy of Citalopram and Amitriptyline in Elderly Depressed Patients Treated in General Practice," Depression and Anxiety, 1998, 147-153, vol. 8, Wiley-Liss, Inc.

(Continued)

Primary Examiner—Ardin Marschel
Assistant Examiner—Leslie A Royds
(74) Attorney, Agent, or Firm—Christie, Parker & Hale, LLP.

(57) ABSTRACT

A method for determining the appropriate medication for a patient suffering from depression. A patient will take a questionnaire wherein the patient answers a number of questions with scaled responses concerning the degree to which the patient's mental state is affected by at least one or both of impaired modulation and impaired activation. Next, the patient's answers will be processed to arrive at scores for the at least one impaired modulation and impaired activation. Depending upon the patient's scores for demodulation and deactivation, at least one medication which affects the at least one impaired modulation and impaired activation is recommended.

10 Claims, 5 Drawing Sheets

OTHER PUBLICATIONS

Lydiard, R. Bruce, "The Role of Drug Therapy in Social Phobia," Journal of Affective Disorders, 1998, vol. 50, S35-S39, Elsevier Science B.V.

Uzunova, V., et al. "Increase in the cerebrospinal fluid content of neurosteroids in patients with unipolar major depression who are receiving fluoxetine or fluvoxamine,," Mar. 1998, 3239-3244, vol. 95, The National Academy of Sciences.

Verkes, Robbert J. et al. "Reduction by Paroxetine of Suicidal Behavior in Patients with, Repeated Suicide Attempts But Not Major Depression," American Journal of Psychiatry, Apr. 1998, 543-547, vol. 155, Issue 4.

Pigott, Teresa A. et al. "A Review of the Efficacy of Selective Serotonin Reuptake Inhibitors in Obsessive-Compulsive Disorder," Journal of Clinical Psychiatry, Feb. 1999, 101-106, vol. 60, Issue 2.

Rampello L., et al. "Dopaminergic hypothesis for retarded depression: a symptom profile for predicting therapeutical responses," Institutes of Neurology and Neurosurgery, University of Catania, Italy, 552-554.

Goodnick, Paul J. et al. "Psychotropic Treatment of Chronic Fatigue Syndrome and Related Disorders," Journal of Clinical Psychiatry, Jan. 1993, 13-20, vol. 54, Issue 1.

Ferguson, James et al. "Bupropion in Tricyclic Antidepressant Nonresponder with Unipolar Major Depressive Disorder," Annals of Clinical Psychiatry, 1994, vol. 6, No. 3, 153-160.

Marin, Robert S. et al. "Apathy: A Treatable Syndrome," Journal of Neuropsychiatry and Clinical Neurosciences, Winter 1995, vol. 7, No. 1, 23-30.

Dubini, Adriana et al. "Noradrenaline-selective versus serotonin-selective antidepressant therapy: differential effects on social functioning," Journal of Psychopharmacology, 1997, vol. 11, No. 4 Supplement, S17-S23.

Montgomery, Stuart A. "Is there a role for a pure noradrenergic durg in the treatment of depression?," European Neuropsychopharmacology, 1997, S3-S9 and S71-S73, vol. 7, Suppl. 1, Elsevier Science B.V.

Cantwell, Dennis P., "ADHD Through the Life Span: The Role of Bupropion in Treatment," Journal of Clinical Psychiatry, 1998, 92-94, vol. 59, Suppl. 4.

Cornelius, Jack R. et al., "Fluoxetine Versus Placebo in Depressed Alcoholic Cocaine Abusers," Psychophamacology Bulletin, 1998, 117-121, vol. 34, No. 1.

Frances, Allen J., et al., "The Expert Consensus Guidelines for Treating Depression in Bipolar Disorder," Journal of Clinical Psychiatry, 1998, 73-79, vol. 59, Supp 4.

Massana, Juan, "Reboxetine Versus Fluoxetine: An Overview of Efficacy and Tolerability," Journal of Clinical Psychiatry, 1998, 8-10, vol. 59, Supp. 14.

Amsterdam, Jay D., et al., "Clomipramine Augmentation in Treatment-Resistant Depression," Depression and Anxiety, 1997, 84-90, vol. 5.

Charney, Dennis S., M.D., "Monoamine Dysfunction and the Pathophysiology and Treatment of Depression," Journal of Clinical Psychiatry, 1998, 11-14, vol. 14, Supp 14.

Nelson, Craig J., "Augmentation Strategies With Serotonergic-Noradrenergic Combinations", Journal of. Clinical Psychiatry 1998, 65-69, vol. 59, Suppl 5.

Nierenberg, Andrew A., et al."Course and Treatment of Atypical Depression", Journal of Clinical Psychiatry, 1998, 5-9, vol. 59, Suppl 18.

Nutt, D. J. "Efficacy of Mirtazapine in Clinically Relevant Subgroups of Depressed Patients", Depression and Anxiety, 1998, 8-10, vol. 7, Suppl 1.

Rudolph, Richard L., et al., "A Meta-Analysis of the Effects of Venlafaxine on Anxiety Associated with Depression," Journal of Clinical Psychopharmacology, 1998, 136-144,vol. 18, No. 2.

Schweitzer, Isaac, et al., "Risk of Adverse Events with the Use of Augmentation Therapy of the Treatment of Resistant Depression", Drug Safety, Dec. 1998, 455-464, vol. 19 (6).

Stahl, Stephen M.,"Selecting an Antidepressant by Using Mechanism of Action to Enhance Efficacy and Avoid Side Effects", Journal of Clinical Psychiatry, 1998, 23-39, vol. 59, Suppl. 18.

Schatzberg, Alan F.,"Antidepressant Effectiveness in Severe Depression and Melancholia", Journal of Clinical Psychiatry, 1999, 14-22, vol. 60, Suppl 4.

Shelton, Richard C.,"Treatment Options for Refractory Depression", Journal of Clinical Psychiatry, 1999, 57-61, vol. 60, Suppl 4.

Åberg-Wistedt, Anna, et al., "Sertraline Versus Paroxetine in Major Depression: Clinical Outcome After Six Months of Continuous Therapy", Journal of Clinical Psychopharmacology, Dec. 2000, 645-652, vol. 20, No. 6.

Ballenger, James C. et al., "Practical Approaches to the Treatment of Panic Disorder", Journal of Clinical Psychiatry, Jan. 1996, 45-52, vol. 57, No. 1.

Ashton, Adam Keller, "Bupropion as an Antidote for Serotonin Reuptake Inhibitor-Induced Sexual Dysfunction", Journal of Clinical Psychiatry, Mar. 1998, 112-115, vol. 59, No. 3.

Barrickman, Les L., "Bupropion versus Methylphenidate in the Treatment of Attention-Deficit Hyperactivity Disorder", Journal American Academy of Child and Adolescent Psychiatry, May 1995, 649-657, vol. 34, No. 5.

Biederman, Joseph,"A Double-blind Placebo Controlled Study of Desipramine in the Treatment of ADD: III. Lack of Impact of Comorbidity and Family History Factors on Clinical Response", Journal American Academy of Child and Adolescent Psychiatry, Jan. 1993, vol. 32, No. 1.

Biederman, Joseph, et al., "A Double-Blind Placebo Controlled Study of Desipramine in the Treatment of ADD: I. Efficacy", American Academy of Child and Adolescent Psychiatry, 1989, 777-784.

Blier, Pierre et al., "Current advances and trends in the treatment of depression", TiPs, Jul. 1994, 220-226, vol. 15.

Bodkin, J. Alexander, et al., "Combining Serotonin Reuptake Inhibitors and Bupropion in Partial Responders to Antidepressant Monotherapy," Journal of Clincial Psychiatry, Apr. 1997, 137-145, vol. 58, No. 4.

Brodie, H. Keith H., et al., "Catecholamines and mania: The effect of alpha-methyl-para-tyrosine on manic behavior and catecholamine metabolism", Clinical Pharmacology and Therapeutics, 218-224, vol. 12, No. 2, Part 1.

Bunney, William E., et al., "Norepinephrine in Depressive Regions", Arch Gen. Psychiat,, Dec. 1965, 483-494, vol. 13.

Carpenter, Linda L., et al., "Tryptophan Depletion During Continuous CSF Sampling in Healthy Humans Subjects", Neuropsychopharmacology, 1998, 26-35, vol. 19, No. 1.

Casat, Charles D., et al., "A Double-Blind Trial of Bupropion in Children With Attention Deficit Disorder", Psychopharmacology Bulletin, 1987, 120-123, vol. 23, No. 1.

Charney, Dennis S., "Receptor Sensitivity and the Mechanism of Action of Antidepressant Treatment", Arch gen Psychiatry, 1981, 1160-1180, vol. 38.

Conners, Keith C., "Bupropion Hydrochloride in Attention Deficit Disorder with Hyperactivity", Journal American Academy of Child and Adolescent Psychiatry, Oct. 1996, 1314-1321, vol. 34, No. 10.

Coppen, Alec, "Tryptophan in the Treatment of Depression", The Lancet, Dec. 2, 1967, 1178-1180.

Danish University Antidepressant Group, "Citalopram: Clinical effect profile in comparison with clomipramine. A controlled multicenter study," Psychopharmacology, 1986, 131-138, vol. 90.

Danish University Antidepressant Group, "Paroxetine: A selective serotonin reuptake inhibitor showing better tolerance, but weaker antidepressant effect than clomipramine in a controlled multicenter study", Journal of Affective Disorders, 1990, 289-299, vol. 18.

Daviss, W. Burleson, et al., "Bupropion Sustained Release in Adolescents With Comorbid Attention-Deficit/Hyperactivity Disorder and Depression", Mar. 2001, 307-314, Journal of American Academy of Children and Adolescent Psychiatry, vol. 40, No. 3.

Delgado, P.L., et al., "Neuroendocrine and Behavioral Effects of Dietary Tryptophan Restriction in Healthy Subjects", Life Sciences, 1989, 2323-2332, vol. 45.

Delgado, Pedro L., et al. "Monoamines and the Mechanism of Antidepressant Action: Effects of Catecholamine Depletion on Mood of Patients Treated with Antidepressants", Psychopharmacology Bulletin, 1993, 389-396, vol. 29, No. 3.

Delgado, Pedro L., et al., "Tryptophan-Depletion Challenge in Depressed Patients Treated with Desipramine or Fluoxetin: Implications for the Role of Serotonin in the Mechanism of Antidepressant Action", Biol Psychiatry, 1999, 212-220, vol. 46.

Duman, Ronald S., et al., "A Molecular and Cellular Theory of Depression", Arch Gen Psychiatry, Jul. 1997, vol. 54.

Fluoxetine Bulimia Nervosa Collaborative Study Group, "Fluoxetine in the Treatment of Bulimia Nervosa", Arch Gen Psychiatry, Feb. 1992, 139-147, vol. 49.

Gelenberg, Alan J., "Efficacy of Venlafaxine Extended-Release Capsules in Nondepressed Outpatients With Generalized Anxiety Disorder", JAMA, Jun. 21, 2000, 3082-3088, vol. 283, No. 23.

Goldstein, David J., "Duloxetin in the Treatment of Major Depressive Disorder: A Double-Blind Clinical Trial", Journal of Clinical Psychiatry, Mar. 2002, 225-231, vol. 63, No. 3.

Goodman, Wayne K., et al., "Specificity of Serotonin Reuptake Inhibitors in the Treatment of Obsessive-Compulsive Disorder", Arch Gen Psychiatry, Jun. 1990, 577-585, vol. 47.

Greist, John H., et al., "Efficacy and Tolerability of Serotonin Transport Inhibitors in Obsessive-Compulsive Disorder", Arch Gen Psychiatry, 53-60, Jan. 1995, vol. 52.

Hall, Sharon M., et al., "Nortriptyline and Cognitive-Behavioral Therapy in the Treatment of Cigarette Smoking", Arch Gen Psychiatry, Arch Gen Psychiatry, Aug. 1998, 683-690, vol. 55.

Healy, David, et al., "The enhancement of social functioning as a therapeutic principle in the management of depression", Journal of Psychopharmacology, 1997, S25-S31, vol. 11, No. 4 Suppl.

Heninger, George R., et al., "$\alpha_2$-Adrenergic Receptor Sensitivity in Depression", Arch Gen Psychiatry, Aug. 1988, 718-726, vol. 45.

Hughes JR., et al., "Antidepressants for Smoking Cessation", Cochrane Review, 2002, Issue 2.

Hunt, Robert D., et al., "An Open Trial of Guanfacine in the Treatment in the Treatment of Attention-Deficit Hyperactivity Disorder", Journal of American Academy of Child and Adolescent Psychiatry, Jan. 1995, 50-54, vol. 34, No. 1.

Hunt, Robert D., "Clonidine Benefits Children with Attention Deficit Disorder and Hyperactivity: Report of a Double-Blind Placebo-Crossover Therapeutic Trial", Journal of the American Academy of Child Psychiatry, 1985, 617-629, vol. 24, No. 5.

Kellner, Robert, et al., "The One-Week Prevalence of Symptoms in Neurotic Patients and Normals", American Journal of Psychiatry, Jan. 1973, 102-105, vol. 130, No. 1.

Kennedy, Sidney H., et al., "Combining Bupropion SR With Venlafaxine, Paroxetin, or Fluoxetine: A Preliminary Report of Pharmacokinetc, Therapeutic, and Sexual Dysfunction Effects," Journal Clinical Psychiatry, Mar. 2002, 181-186, vol. 63, No. 3.

Kessler, Ronald C., et al. "Lifetime and 12-Month Prevalence of DSM-III-R Psychiatric Disorders in the United States", Arch Gen Psychiatry, Jan. 1994, 8-19, vol. 51.

Kessler, R.C., et al. "Comorbidity of DSM-III-R Major Depressive Disorder in the General Population: Results from the US National Comorbidity Survey", British Journal of Psychiatry, 1996, 17-30, vol. 168, Suppl. 30.

Kihara, Tsuyoshi, et al., "Effects of Duloxetine, a New Serotonin and Norepinephrine Uptake Inhibitor, on Extracellular Monoamine Levels in Rat Frontal Cortex", The Journal of Pharmacology and Experimental Therapeutics, 1995, 177-183,vol. 272, No. 1.

Kirsch, Michael A., et al., "Combination Treatment With Venlafaxine and Bubpropion", American Journal of Psychiatry, Mar. 1999, 494, vol. 156, No. 3.

Labbate, Lawrence A., et al., "Bupropion Treatment of Serotonin Reuptake Antidepressant-Associated Sexual Dysfunction", Annals of Clinical Psychiatry, 1997, 241-245, vol. 9, No. 4.

Malberg, Jessica E., et al., "Chronic Antidepressant Treatment Increases Neurogenesis in Adult Rat Hippocampus", The Journal of Neuroscience, Dec. 15, 2000, 9104-9110, vol. 20(24).

Marshall, Randall D., et al., "Paroxetine/Bupropion Combination Treatment for Refractory Depression", Journal of Clinical Psychopharmacology, Feb. 1996, 80-81, vol. 16, No. 1.

McDougle, Christopher J., et al., "A Double-blind, Placebo-Controlled Study of Risperidone Addition in Serotonin Reuptake Inhibitor-Refractory Obsessive-compulsive Disorder", Arch Gen Psychiatry, Aug. 2000, 794-801, vol. 57.

McDougle, Christopher J., et al., "Haloperidol Addition in Fluvoxamine-Refractory Obsessive-Compulsive Disorder", Arch Gen Psychiatry, Apr. 1994, 302-308, vol. 51.

Mega, Michael S., et al., "The Limbic System: An Anatomic, Phylogenetic, and Clinical Perspective", Journal of Neuropsychiatry, Summer 1997, 315-330, vol. 9, No. 3.

Michelson, David, et al., "Atomoxetine in the Treatment of Children and Adolescents with Attention-Deficit/Hyperactivity Disorder: A Randomized, Placebo-Controlled, Dose-Response Study", Pediatrics, American Academy of Pediatrics, Nov. 2001, e83, 1197, vol. 108, No. 5.

Miller, Helen L., et al., "Clinical and Biochemical Effects of Catecholamine Depletion on Antidepressant-Induced Remission of Depression", Arch Gen Psychiatry, Feb. 1996, 117-128, vol. 53.

Modigh, Kjell, et al., "Superiority of Clomipramine over Imipramine in Treatment of Panic Disorder: A Placebo-Controlled Trial", Journal of Clinical Psychopharmacology, Aug. 1992, vol. 12, No. 4l.

Montejo, Angel L., et al., "Incidence of Sexual Dysfunction Associated With Antidepressant Agents: A prospective Multicenter Study of 1022 Outpatients", Journal of Clinical Psychiatry, 2001, 10-21, vol. 62, Suppl. 3.

Nelson, J. Craig, "A Review of the Efficacy of Serotonergic and Noradrenergic Reuptake Inhibitors for Treatment of Major Depression", Biol. Psychiatry, 1999, 1301-1308-, vol. 46.

Nibuya, Masashi, et al., "Regulation of BDNF and trkB mRNA in Rat Brain by Chronic Electroconvulsive Seizure and Antidepressant Drug Treatments," The Journal of Neuroscience, Nov. 1995, 7539-7547, vol. 15(11).

Paul, Ian A., et al., "Adaptation of the N-Methyl-D-Aspartate Receptor Complex Following Chronic Antidepressant Treatments", The Journal of Pharmacology and Experimental Therapeutics, Dec. 29, 1993, vol. 269, No. 1.

Pollack, Mark H., et al., "Paroxetine in the Treatment of Generalized Anxiety Disorder: Results of a Placebo-Controlled, Flexible -Dosage Trial", Journal of Clinical Psychiatry, May 2001, vol. 62, No. 5.

Prince, Jefferson B., "A Controlled Study of Nortriptyline in Children and Adolescents with Attention Deficit Hyperactivity Disorder", Journal of Child and Adolescent Psychiatry, 2000, 193-204, vol. 10, No. 3.

Prince, Jefferson B., "Clonidine for Sleep Disturbances Associated with Attention-Deficit Hyperactivity Disorder: A Systematic Chart Review of 62 Cases", Journal Am. Acad. Child Adolesc. Psychiatry, May 1996, 599-605, vol. 35, No. 5.

Prochazka, Allan V., "A Randomized Trial of Nortriptyline for Smoking Cessation", Arch. Intern Med., Oct. 12, 1998, 2035-2039, vol. 158.

Sanacora Gerard, et al., "Increased Occipital Cortex GABA Concentrations in Depressed Patients After Therapy With Selective Serotonin Reuptake Inhibitors", Am J. Psychiatry, Apr. 2002, 663-665, vol. 159, No. 4.

Scahill Larry, et al., "A Placebo-Controlled Study of Guanfacine in the Treatment of Children With Tic Disorders and Attention Deficit Hyperactivity Disorder", Am J Psychiatry, Jul. 2001, 1067-1074, vol. 158, No. 7.

Schildkraut, Joseph J., "The Catecholamine Hypothesis of Affective Disorders: A Review of Supporting Evidence", The American Journal of Psychiatry, Nov. 1965, 509-523, vol. 122.

Slemmer, Jennifer E., "Bupropion Is A Nicotinic Antagonist", The Journal of Pharmacology and Experimental Therapeutics, 2000, 321-327, vol. 295, No. 1.

Spencer, Thomas, "Pharmacotherapy of Attention-Deficit Hyperactivity Disorder Across the Life Cycle", J. Am. Acad. Child Adolesc. Psychiatry, Apr. 1996, 409-432, vol. 35, No. 4.

Spier, Scott A., "Use of Bupropion with SRIs and Venlafaxine", Depression and Anxiety, 1998, 73-75, vol. 7.

Stein, Murray B., "Paroxetine Treatment of Generalized Social Phobia (Social Anxiety Disorder)", JAMA, Aug. 26, 1998, 708-713, vol. 280, No. 8.

Steiner, Meir, et al., "Fluoxetine in the Treatment of Premenstrual Dysphoria", The New England Journal of Medicine, Jun. 8, 1995, 1529-1534, vol. 332, No. 23.

Thase, Michael E., "Remission rates during treatment with Venlafaxine or selective serotonin reuptake inhibitors", British Journal of Psychiatry, 2001, 234-241, vol. 178.

Uhde, Thomas W., "Phenomenology and Neurobiology of Social Phobia: Comparison With Panic Disorder", J Clinical Psychiatry, Nov. 1991, 31-40, vol. 52, No. 11.

Wender, Paul H., "Bupropion Treatment of Attention-Deficit Hyperactivity Disorder in Adults", Aug. 1990, 1018-1020, Am J Psychiatry vol. 147, No. 8.

Wheatley, David P., "Mirtazapine: Efficacy and Tolerability in Comparison With Fluoxetine in Patients with Moderate to Severe Major Depressive Disorder", J Clinical Psychiatry, Jun. 1998, 306-312, vol. 59, No. 6.

Wilens, Timothy E., "Six-Week, Double-blind, Placebo-Controlled Study of Desipramine for Adult Attention Deficit Hyperactivity Disorder", Sep. 1996, 1147-1153, Am J Psychiatry, vol. 153, No. 9.

Wilens, Timothy E., "A Controlled Clinical Trial of Bupropion for Attention Deficit Hyperactivity Disorder in Adults", Feb. 2001, Am J Psychiatry, 282-288, vol. 158, No. 2.

Wilens, Timothy E., "Combining Methylphenidate and Clonidine: A Clinically Sound Medication Option", J. AM. Acad. Child Adolesc. Psychiatry, May 1999, vol. 38, No. 5.

Williams, W. A., "Effects of Acute Tryptophan Depletion of Plasma and Cerebrospinal Fluid Tryptophan and 5-Hydroxyindoleacetic Acid in Normal Volunteers", Journal of Neurochemistry, 1999, 1641-1647, vol. 72, No. 4.

European Neuropsychopharmacology, sciencedirect.com, "Reboxetine plus citallopram in treatment resistant depression," P.1.152, vol. 10, Supplement 3, (Sep. 2000).

European Neuropsychopharmacology, sciencedirect.com, "Coadministration therapy with reboxetine and serotonin specific reuptake inhibitors in twenty-four patients with major depression," P.1.034, vol. 10, Supplement 3, (Sep. 2000).

* cited by examiner

TARGETED TREATMENT DEPRESSION INVENTORY (TTDI)

Date ___/___/___  Pt. Initials _____________  Pt. Master # __________
Name of study __________ Clinician _______ Ham-D Score _________
Current Med ______________ How long? _________ Current dose ______
Prior TTDI scores: M____ A___ D____ Date _____________
                      M____ A___ D____ Date _____________
                      M____ A___ D____ Date _____________

Please ⟨circle⟩ the one choice for each item that best describes you during the past few weeks compared to your "usual" (healthiest and most "normal") self.
If you have never felt "normal" in your entire life, compare how you have felt during the past few weeks to your idea of how healthy people usually feel.
If you have had many ups and downs recently, answer each item as best you can according to how you have felt in general.

1. I've been anxious
   *a lot less than usual*  *somewhat less than usual*  *the same as usual*  *somewhat more than usual*  *a lot more than usual*

2. I've felt energetic
   *a lot less than usual*  *somewhat less than usual*  *the same as usual*  *somewhat more than usual*  *a lot more than usual*

3. I've been angry
   *a lot less than usual*  *somewhat less than usual*  *the same as usual*  *somewhat more than usual*  *a lot more than usual*

4. I've felt motivated
   *a lot less than usual*  *somewhat less than usual*  *the same as usual*  *somewhat more than usual*  *a lot more than usual*

5. My health has worried me
   *a lot less than usual*  *somewhat less than usual*  *the same as usual*  *somewhat more than usual*  *a lot more than usual*

FIG. 3

| | | | | |
|---|---|---|---|---|
| 6. People have annoyed me | | | | |
| *a lot less than usual* | *somewhat less than usual* | *the same as usual* | *somewhat more than usual* | *a lot more than usual* |
| 7. I've experienced enjoyment | | | | |
| *a lot less than usual* | *somewhat less than usual* | *the same as usual* | *somewhat more than usual* | *a lot more than usual* |
| 8. I've felt agitated | | | | |
| *a lot less than usual* | *somewhat less than usual* | *the same as usual* | *somewhat more than usual* | *a lot more than usual* |
| 9. I've taken initiative | | | | |
| *a lot less than usual* | *somewhat less than usual* | *the same as usual* | *somewhat more than usual* | *a lot more than usual* |
| 10. I've lost control of my emotions | | | | |
| *a lot less than usual* | *somewhat less than usual* | *the same as usual* | *somewhat more than usual* | *a lot more than usual* |
| 11. I've slept | | | | |
| *a lot less than usual* | *somewhat less than usual* | *the same as usual* | *somewhat more than usual* | *a lot more than usual* |
| 12. I've eaten | | | | |
| *a lot less than usual* | *somewhat less than usual* | *the same as usual* | *somewhat more than usual* | *a lot more than usual* |
| *13.* I've had good concentration | | | | |
| *a lot less than usual* | *somewhat less than usual* | *the same as usual* | *somewhat more than usual* | *a lot more than usual* |
| 14. I've thought about death | | | | |
| *a lot less than usual* | *somewhat less than usual* | *the same as usual* | *somewhat more than usual* | *a lot more than usual* |
| 15. I've felt productive | | | | |
| *a lot less than usual* | *somewhat less than usual* | *the same as usual* | *somewhat more than usual* | *a lot more than usual* |

FIG. 3 (Cont.)

16. If I were to take medication now, I would want it to help me feel
    *a lot calmer*        *somewhat calmer*        *no calmer than usual*

17. If I were to take medication now, I would want it to help me feel
    *a lot more energetic*        *somewhat more energetic*        *no more energetic than usual*

Circle an answer for these items if this is your first time taking this test.

18. During my life I have wanted to feel calmer than I was
    *a lot of the time*        *sometimes*         *rarely*

19. During my life I have wanted to feel more energetic than I was
    *a lot of the time*        *sometimes*         *rarely*

METHOD FOR THE TARGETED TREATMENT OF DEPRESSION

BACKGROUND OF THE INVENTION

The invention relates to clinical depression, the leading cause of medical disability in the world, and more specifically to a method for determining what antidepressant regimen is best suited for a patient with depression.

Presently, there are few guidelines for determining the appropriate agents to use in treating depressed patients. Traditional thinking holds that all antidepressants are the same except for side-effects. This assumption is based on the fact that all antidepressants show approximately the same level of effectiveness (50-70%) in studies on undifferentiated depressed populations. However, recent investigations which differentiate between subtypes of depression indicate that matching antidepressants with specific subtypes can improve results. Unfortunately, none of the depression assessment tools currently available identify these subtypes (e.g., DSM-IV-TR, Hamilton, Beck, Montgomery-Asberg, Zung). Thus, many health professionals seeing such patients fail to make the proper diagnosis and, when they attempt to treat may not always use medications optimally.

There accordingly remains a need for an improved method that permits even inexperienced providers to quickly, easily, inexpensively, and accurately determine which type of depression is present (e.g. whether the depression is primarily characterized by (1) impaired CNS modulation, with typical symptoms of anxiety, irritability, hostility, impulsivity, agitation, hypochondriasis, or suicidality; (2) impaired activation, with common symptoms of fatigue, apathy, anhedonia, hypersomnia, lack of initiative, inability to concentrate, and decreased productivity, or (3) a combination of both types) and to prescribe the treatment regimen that is most likely to lead to clinical improvement.

A half century ago the discovery that depression was often improved by medications affecting monoamine neurotransmitters led to several optimistic "one disease-one neurotransmitter" theories. The norepinephrine and serotonin hypotheses of depression posited simple synaptic deficiencies of these chemicals as the basis of depression. Advances in neuroscience and more rigorous clinical research ultimately demonstrated problems with these theories, such as delays in clinical improvement until weeks or months after correction of putative synaptic deficiencies and the comparable efficacies in undifferentiated depressed populations. By the end of the $20^{th}$ century, identification of complex intraneuronal pathways involving multiple signaling systems and neuroadaptive genetic transcription mechanisms seemed to offer more compelling explanatory possibilities. Thus, most practitioners have been encouraged to believe that differences between serotonergic and catecholaminergic antidepressants are of little importance.

The concept of "targeted treatment" in depression, i.e., the use of a particular class of antidepressant against a particular depressive subtype, had until recently found little scientific support. Over a quarter century ago Klein and his co-workers showed "dirty" antidepressants such as tricyclics and monoamine oxidase inhibitors's (MAOI'S) to be somewhat more beneficial in melancholia and a typical depression, respectively. However, since 1988, with the introduction of "cleaner" agents like fluoxetine (Prozac and others), selective serotonin reuptake inhibitors (SSRI's) have demonstrated higher efficacies than catecholaminergic agents in treating many disorders such as anxiety, panic, phobias, postraumatic stress (PTSD), premenstrual disorder (PMS) and obsessive-compulsive disorder (OCD). On the other hand, catecholaminergic agents such as bupropion (Wellbutrin) and reboxetine have shown greater effectiveness in restoring energy, motivation and libido. Supporting the idea that neurotransmitter mechanisms matter, depletion experiments have shown that the condition of a successfully treated depressed patient will worsen if depleted of the neurotransmitter that his or her antidepressant treatment has targeted, but not if other neurotransmitters are depleted. Similarly, pre-treatment Q-EEG measurements can predict whether depressed patients will respond to a serotonergic as opposed to another type of antidepressant. In severe depressions, dual mechanism regimens (serotonergic and catecholaminergic) are more effective than monotherapies.

Because of the potential clinical importance of targeting, the inventor has been studying and matching selective serotonergic and catecholaminergic antidepressants to particular subtypes of depression for over a decade. The naturalistic outpatient study on which the invention is based involved 1000 depressed patients. In a random sample of 100 patients who were treated according to the invention's targeting algorithm, 96% were improved (CGI ratings <3) compared with 65% given standard non-targeted treatment (n=55). More recently, 12 patients who received the wrong treatment according to the invention exhibited only 29% as much improvement as 84 people treated according to the invention's recommendations.

Embodying the knowledge gained in these studies, the invention provides clinicians in diverse settings with a rapid, user-friendly method for selecting antidepressants that are more likely to prove effective.

SUMMARY OF THE INVENTION

The invention provides a new treatment-oriented method of characterizing the primary depressive subtypes.

The invention further provides a method of detecting and quantifying those subtypes.

The invention also provides a non-invasive method for determining which type of antidepressant (serotonergic, catecholaminergic or dual-mechanism) is most likely to improve that subtype of depression.

The invention yet further provides a method for determining when to modify or discontinue the initial treatment regimen.

The invention also provides a method for optimizing dosages of antidepressant medications.

The invention additionally provides a method for warning professionals when the potential for suicidal behavior has been detected.

The invention uses a bipolar scale to represent the range from depression to euthymia to mania.

In addition, the invention provides both manual paper and pencil and computerized formats for achieving its objectives.

Other features and advantages of the invention will be apparent from the following description of the preferred embodiments hereof, and from the claims.

DETAILED DESCRIPTION OF THE INVENTION

Figure 1:
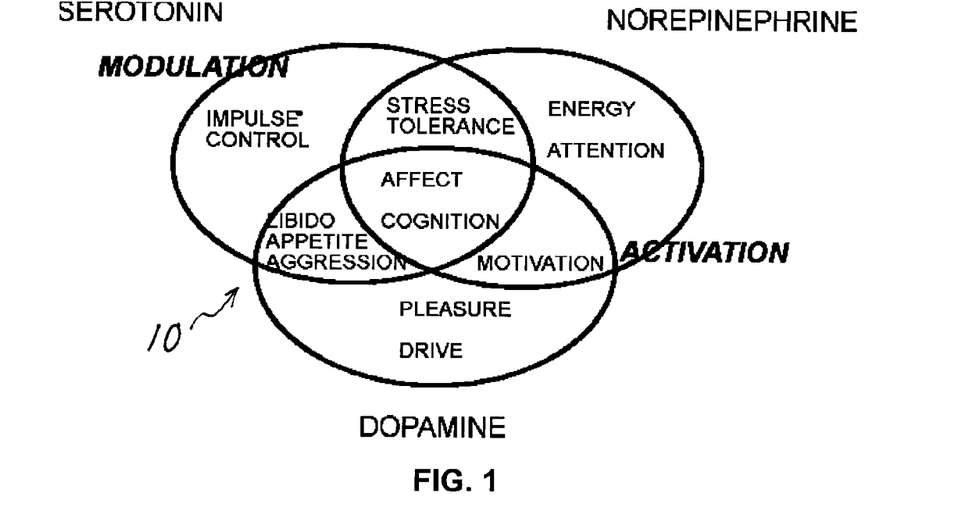
FIG. 1 is a Venn diagram, showing the modulatory effects of serotonin and the activating effects of the catecholamines (norepinephrine and dopamine) in normal human functioning.

FIG. 1 is a Venn diagram showing the modulatory effects of serotonin and the activating effects of the catecholamines (norepinephrine and dopamine) in normal human functioning without depression.

Figure 2:
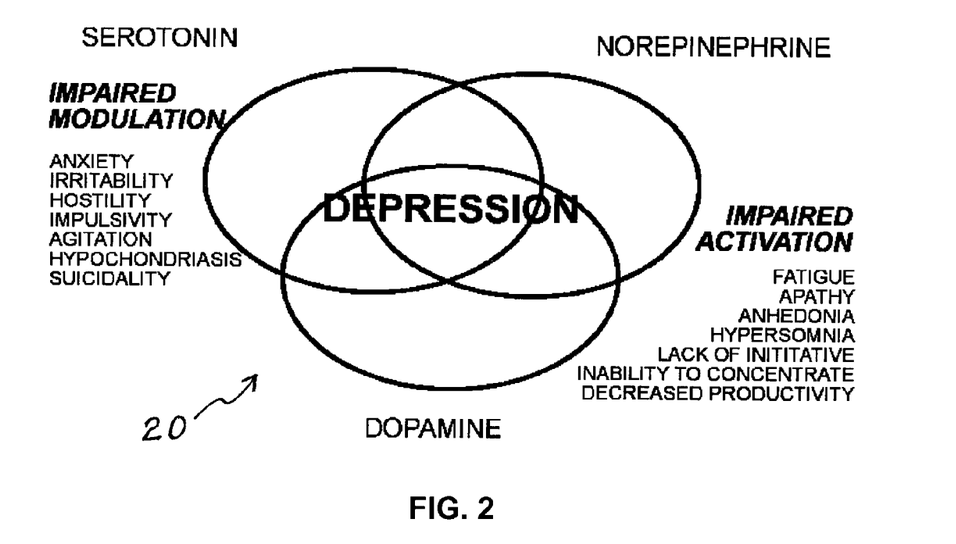
FIG. 2 is Venn diagram showing the symptoms of impaired modulation and activation secondary to reduced serotonin, norepinephrine and dopamine neurotransmission in depression.

FIG. 2 is Venn diagram showing the symptoms of impaired modulation and activation secondary to reduced serotonin, norepinephrine and dopamine neurotransmission in depression.

Table 1 shows the serotonergic, noradrenergic and dopaminergic activity of some of the commonly available and more selective antidepressant medications.

TABLE 1

| GENERIC/ BRAND | SEROTONIN | NOREPINEPHRINE | DOPAMINE |
|---|---|---|---|
| BUPROPION/ WELLBUTRIN | | X | X |
| CITALOPRAM/ CELEXA | X | | |
| FLUOXETINE/ PROZAC | X | | |
| FLU-VOXAMINE/ LUVOX | X | | |
| MIRTAZPINE/ REMERON | X | X | |
| PAROXETINE/ PAXIL | X | X | |
| SERTRALINE/ ZOLOFT | X | | X |
| VENLAFAXINE/ EFFEXOR | X | X | |

Table 2 shows the clinical features of the depressive subtypes.

Figure 3:
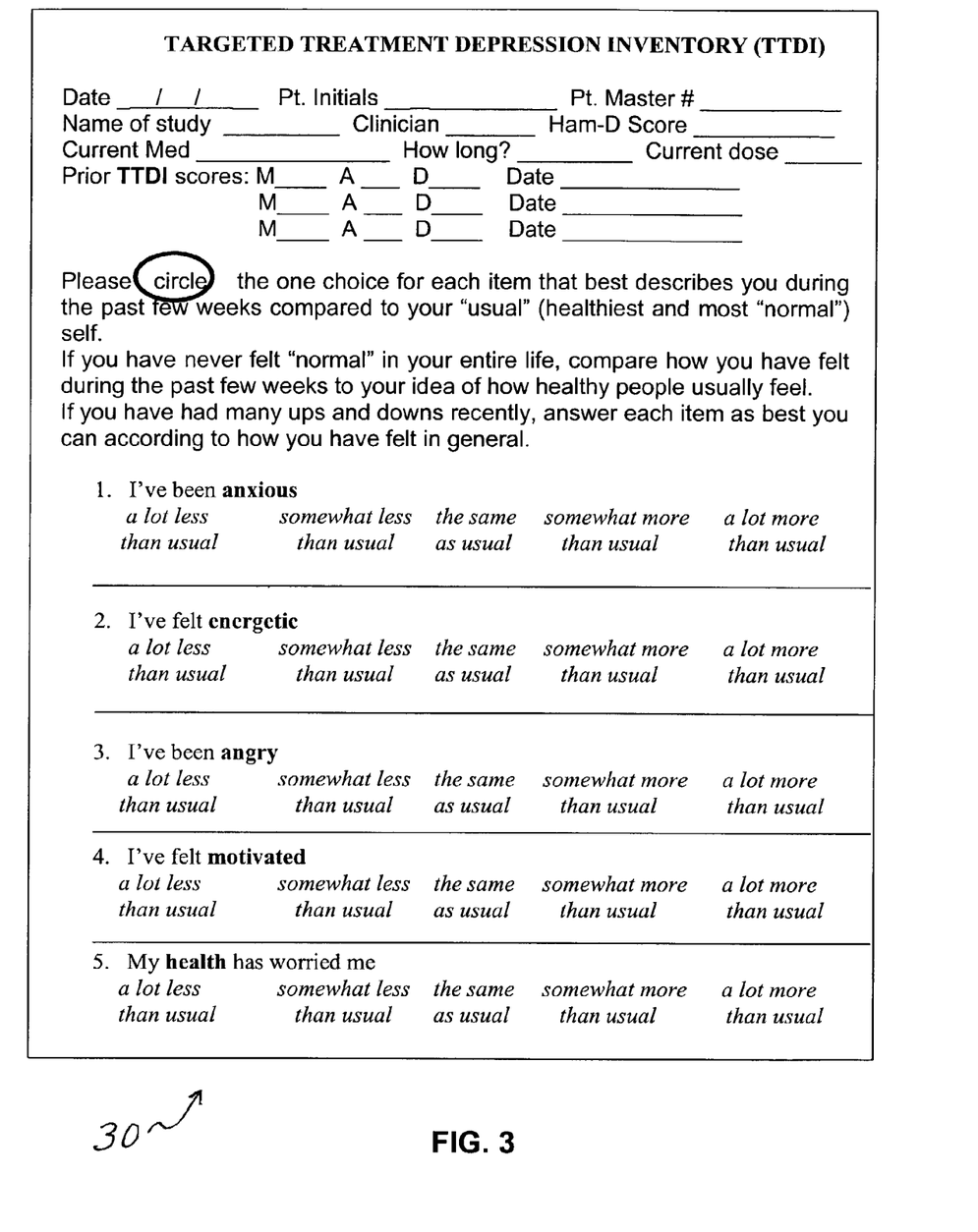
FIG. 3 depicts the scoring sheet of the invention in its self-administered "paper and pencil" version.

FIG. 3 depicts an embodiment of the invention in its self-administered "paper and pencil" version.

The formula for calculating M and A scores from Items 1-17 (I1-I17) of FIG. 3 is as follows:

$$M = I1 + I3 + I5 + I6 + I8 + I10 - I11 - I12 + I14 + I16 \quad \text{Formula 1}$$

$$A = -I2 - I4 - I7 - I9 + I11 + I12 - I13 - I15 + I17 \quad \text{Formula 2}$$

Table 4 demonstrates an exemplary programming script for calculating the M and A scores on a Palm Pilot handheld computer utilizing a proprietary database management system for the Palm operating system. Alternate programs can be used for other personal digital assistants, handheld computers, laptop computers, and other computerized devices.

TABLE 4

| M calculation: | A calculation: |
|---|---|
| result = $4 + $6 | result = result − $5 |
| result = result + $8 | result = result − $7 |
| result = result + $9 | result = result − $10 |
| result = result + $11 | result = result − $12 |
| result = result + $13 | result = result + $14 |
| result = result − $14 | result = result + $15 |
| result = result − $15 | result = result − $16 |
| result = result + $17 | result = result − $18 |
| result = result + $19 | result = result + $20 |
| answer = result − 15 | answer = result + 12 |

Embodiment A—Standard 17—Item Form

Turning now to a further description, in EMBODIMENT A of the invention, a 17-item (plus 2 historical or "H" items) multiple choice test that identifies and quantifies two dimensions which have been found by the inventor to correlate with

TABLE 2

| SUBTYPE | REACTIVITY | ENERGY | SLEEP | APPETITE |
|---|---|---|---|---|
| DEMODULATED | INCREASED | SAME OR INCREASED | DECREASED | DECREASED |
| DEACTIVATED | DECREASED | DECREASED | INCREASED | SAME OR INCREASED |
| MIXED | VARIABLE | VARIABLE | VARIABLE | VARIABLE |

Table 3 shows the relationship between TTDI scores and depressive subtypes.

TABLE 3

| SUBTYPE | STANDARD NAMES | M SCORE | A SCORE | D SCORE |
|---|---|---|---|---|
| DEMODULATED | ANXIOUS AGITATED HOSTILE HYPOCHONDRIACAL | ELEVATED | NORMAL OR LOW | ELEVATED |
| DEACTIVATED | PSYCHOMOTOR-RETARDED BLUNTED APATHETIC | NORMAL OR LOW | ELEVATED | ELEVATED |
| MIXED | MELANCHOLIC ATYPICAL REFRACTORY | ELEVATED | ELEVATED | ELEVATED | the need for serotonergic and catecholaminergic antidepressants, respectively. These questions are as follows, and are weighted as follows:

1. I've been anxious
a lot less than usual (−2), somewhat less than usual (−1), the same as usual (0), somewhat more than usual (+1), or a lot more than usual (+2)

Questions 2-15 have the same possible response possibilities as question 1, and are as follows:
2. I've felt energetic . . .
3. I've been angry . . .
4. I've felt motivated
5. My health has worried me . . .
6. People have annoyed me . . .
7. I've experienced enjoyment . . .
8. I've felt agitated . . .
9. I've taken initiative . . .
10. I've lost control of my emotions . . .
11. I've slept . . .
12. I've eaten . . .
13. I've had good concentration . . .
14. I thought about death . . .
15. I've felt productive . . .

Questions 16 and 17 have a different scoring criteria, as follows
16. If I were to take medication now, I would want it to help me feel . . .
a lot calmer (+4), somewhat calmer (+2), no calmer than usual (0)
17. If I were to take medication now, I would want it to help me feel . . .
a lot more energetic (+4), somewhat more energetic (+2), no more energetic than usual (0)

The dimensions are called the M score, measuring the need for central nervous system (CNS) modulation, and the A score, measuring the need for CNS activation. The scores can range as high as +34 or as low as −26 with 0 representing normal. Positive scores tend to be directly proportional to the degree of depressive pathology present and the dosage of medication that may be required. Small negative scores usually reflect better than average functioning, while large negative scores can reflect bipolar pathological states such as mania. An M and/or A score in the range of −1 to −5 indicates that the patient is functioning at a better level of modulation and/or activation, respectively, than usual. An A score ranging from −5 to −9 suggests the presence of hypomania and an A score ranging −10 to −26 suggests the presence of mania.

In a typical application of the invention, a health professional administers the test to a patient in an outpatient or hospital treatment setting. When administered in its non-computerized form (FIG. 3), the test is scored by comparing the patient's paper and pencil responses to a printed scoring key or by inputting the manual responses into computer containing the invention's software program. When administered using a touch-screen monitor, keyboard or PDA powered by that software, the patient's scores and recommended treatment parameters can be provided instaneously to the treating professional.

The test is divided into ten M items that measure impaired modulation and nine A items that measure reduced activation. As shown in Eormulas 1 and 2, the two items included in both series (11. I've slept . . . 12. I've eaten . . . ) affect scores in opposite directions, i.e., sleeping excessively adds 2 to the A score and subtracts 2 from the M score and eating excessively adds 2 to the A score and subtracts 2 from the M score. When positive, the historical items 18 and 19 may add weight to the treatment recommendations, but are not included in the M or A scores, which reflect current states only.

When patients first seek treatment these scores typically reflect the overall level of depression. This is quantified as the D score, which equals the total of the positive M and A scores. Negative M and A scores are not permitted to lower the D score because the severity of a depressive subtype is not reduced by lack of symptoms in a non-contributory dimension. For example, a patient whose A score is elevated is no less depressed simply because his or her ability to manifest anger or irritability (components of the M score) is less than usual. The negative M score in such a case may actually be a function of the reduced energy associated with severe DEACTIVATION.

Scoring Examples:
(a) If M=12 and A=11, then D=23. This would be an example of the MIXED subtype.
(b) If M=−3 and A=14, then D=14. This would be an example of the DEACTIVATED subtype.
(c) If M=15 and A=+1, then D=16. This would be an example of the DEMODULATED subtype.

While the D score resembles the scores derived on traditional unidimensional depression tests such as the Hamilton Depression Inventory, the M and A subscales are unique. When the M score is greater than 4 the invention classifies the patient as DEMODULATED and recommends treatment with a serotonergic antidepressant. Correspondingly, when the A score is greater than 4 the invention identifies the patient as DEACTIVATED and recommends treatment with a catecholaminergic antidepressant. When both M and A scores are above 4 the invention diagnoses a MIXED state and calls for dual-mechanism antidepressant treatment. No other depression test that the inventor is aware of offers this type of pharmacological guidance.

To add even more clinical usefulness, there are three levels of severity associated with each state: MILD, MODERATE AND SEVERE. MILD states are defined as those with M or A scores from 5 to 9. MODERATE states are those with M or A scores from 10 to 14. SEVERE states have M or A scores of 15 or more. Recommended treatment dosages increase with level of severity.

The test is usually repeated two to four weeks after receiving treatment to assess improvement. If the medication is working, the difference between the patient's present condition and his baseline "normal" state will have decreased, resulting in D, M and A scores approaching 0. If that is not the case, as for example when a DEMODULATED patient (elevated M score only) has become secondarily DEACTIVATED by his SEROTONERGIC medication (decreased M score, newly elevated A score), the invention recommends treating this effect of initial treatment with the appropriate agent (e.g., combining the SEROTONERGIC agent with a CATECHOLAMINERGIC antidepressant), typically resulting in improvement or recovery within a few weeks.

Again, the five possible responses to Items 1 through 15 are weighted either: −2, −1, 0, +1 and +2 (M items) or +2, +1, 0, −1, or −2 (A items). For example, Item 1, an M item, is scored as follows

| I've been anxious | | | | |
|---|---|---|---|---|
| a lot less than usual | somewhat less than usual | the same as usual | somewhat more than usual | a lot more than usual |
| −2 | −1 | 0 | +1 | +2 |

Feeling a lot MORE anxious than usual (the DEMODULATED response) raises the M score by 2, whereas feeling a lot LESS anxious than usual (the more MODULATED response) lowers it by 2. Feeling the SAME as usual leaves the score unaffected.

Item 2, an A item, is scored the opposite way:

| I've felt energetic | | | | |
|---|---|---|---|---|
| a lot less than usual | somewhat less than usual | the same as usual | somewhat more than usual | a lot more than usual |
| +2 | +1 | 0 | −1 | −2 |

Feeling a lot MORE energetic than usual (the more ACTIVATED response) LOWERS the A score by 2, while being a lot LESS energetic than usual (the DEACTIVATED response) RAISES it by 2. The invention reverses the choices associated with increased pathology on the two scales in this manner to reduce false positive and negative errors caused by the repetitive selection of the same choice and to provide an immediate indication to the clinician of discrepancies between test-taking behavior and clinical manifestations of deactivation and/or demodulation.

Items 16 and 17 have only 3 choices, but are weighted more heavily than the other items. Item 16 contributes to the M score as shown:

| If I were to take medication now, I would want it to help me feel | | |
|---|---|---|
| a lot calmer | somewhat calmer | no calmer than usual |
| +4 | +2 | 0 |

Item 17 contributes similarly to the A score:

| If I were to take medication now, I would want it to help me feel | | |
|---|---|---|
| a lot more energetic | somewhat more energetic | no more energetic than usual |
| +4 | +2 | 0 |

Methods for calculating the total M and A scores are shown in Formulas 1 and 2, respectively, for a paper and pencil calculation, and in Table 4, which is a program script for a calculating the M and A scores on a Palm Pilot® handheld computer utilizing a proprietary database management system for the Palm operating system. In Table 4, the "$" symbol designates field values followed by a number equal to the item number +3, e.g., "$4" is the raw score for Item 1. Raw scores, which are a function of the requirements of the software used, are corrected when necessary by adding or subtracting the difference between raw and real scores, which in this example is −15 for the M score and +12 for the A score. (These compensatory calculations are required in this case because the Palm Pilot® database management system restricts the 5 choices per item to the integers 1 through 5 rather than −2 through +2.)

Figure 4:
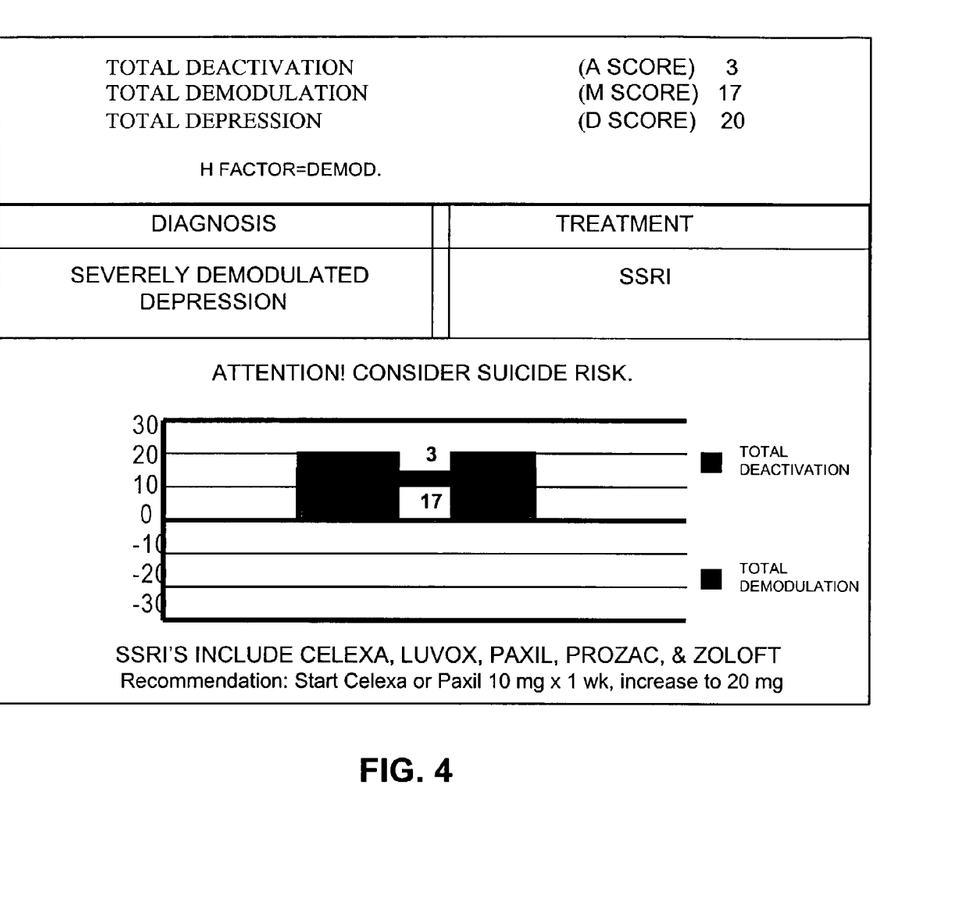
FIG. 4 depicts an exemplary screenprint of the invention's scoring screen in a Windows or Macintosh-based operating system.

Other programming platforms used by the invention, e.g., on Windows and Macintosh computers, utilize other scoring algorithms to arrive at identical results. Moreover, because of their larger screens, laptop and desktop computers can offer more detailed graphic and text-based information in connection with the invention's, software, an example of which is shown in FIG. 4.

For example, when a score of +1 or +2 is obtained for Item 14 (thinking about death "somewhat" or "a lot more than usual"), a warning message appears on the screen to evaluate the patient's suicidal potential with language proportional to the potential danger, and color graphics are used to reinforce these warnings. The invention graphically depicts changes over time in the patient's condition, permitting monitoring and modification of treatment as needed.

Embodiment B—Short Form

EMBODIMENT B of the invention utilizes items 11, 16 and 17 plus two more M and two A scale items ("$IM^x$", "$IM^y$", "$IA^x$", "$IA^y$") to guide treatment. $IM^x$, $IM^y$, $IA^x$ and $IA^y$ can be selected by the professional user during the software set up process. The formulas for calculating M and A scores in this version are:

$$M = 2(IM^x + IM^y - I11 + I16)$$ Formula 3

$$A = 2(IA^x + IA^y + I11 + I17)$$ Formula 4

Multiplying by 2 brings the scores derived in EMBODIMENT B into the same range as those of EMBODIMENT A. While this shorter form may be less comprehensive and accurate than the 17 item version, it can still provide useful guidance in selecting and managing antidepressant treatment. It further offers the professional an opportunity to abbreviate and customize the test to fit his own practice needs.

Embodiment C—Psychobiological Form

In its psychobiological form, the invention utilizes data from physiological measures such as the Q-EEG, serum platelet serotonin assay, and the urinary MHPG to derive the M and A scores. While at the present time, these methods are far more expensive and cumbersome than EMBODIMENTS A and B, new developments in neuroscience suggest that more cost-effective methods will soon be available. These approaches will utilize the principle on which the invention is based, i.e., inferring CNS serotonin and catecholamine levels to determine the most effective antidepressant treatment, by measuring various physical concomitants of that neurotransmitter activity. For example, recent work in neurogenetics suggests that it may soon be possible for physicians to determine in seconds whether patients have the diathesis (genetic tendency) for serotonin or catecholamine impairment or both. The invention will provide a method for doctors to combine or substitute such physical data for the clinical data derived using the items in FIG. 3.

The present invention covers the modifications and variations of this invention provided they come within the scope of the appended claims and their equivalents. In this context, equivalents mean each and every implementation for carrying out the functions recited in the claims, even those not explicitly described herein.

What is claimed is:

1. A method for determining the appropriate medication for a patient suffering from depression, comprising:
   (i) having a patient take a questionnaire wherein the patient answers questions 1 to 17 as set forth in FIG. 3 herein with scaled responses as set forth in FIG. 3 concerning the degree to which the patient's mental state is affected by demodulation and/or deactivation;
   (ii) processing the patient's answers to arrive at scores for the demodulation and/or deactivation;
   wherein said processing step is performed via the following steps:
      the questions 1-15 as set forth in FIG. 3 concern the patient's demodulation and/or deactivation and are scored as very high for answers that the patient feels a lot more of the question, high for answers that the patient feels somewhat more of the question, average for the patient feels the same as usual of the question, low for answers that the patient feels somewhat less of the question, and very low for answers that the patient feels a lot less of the question;

wherein for questions 1 to 15 as set forth in FIG. 3, very high scores are equal to a score of +2; high scores are equal to a score +1; average scores are equal to a score of 0; low scores are equal to a score of −1; and very low scores are equal to a score of −2;

wherein for questions 16 and 17 as set forth in FIG. 3, an answer of a lot more is rated as +4; somewhat more is rated as +2; and no more than usual is rated as 0;

and further wherein a calculation for possible demodulation M is given by the formula $$M=I1+I3+I5+I6+I8+I10-I11-I12+I14+I16,$$

wherein I1, I3, I5, I6, I8, I10, I11, I12, I14 and I16 are the scores for the questions 1, 3, 5, 6, 8, 10, 11, 12, 14 and 16, respectively, as scored in (A) to determine an M score, and wherein an M score of 15 or more indicates severe demodulation, an M score of between 10 to 14 indicates moderate demodulation, an M score of between 5 to 9 indicates mild demodulation, and an M score of 4 or less indicates no significant demodulation;

and wherein a calculation for possible deactivation A is given by the formula $$A=-I2-I4-I7-I9+I11+I12-I13-I15+I17,$$

wherein I2, I4, I7, I9, I11, I12, I13, I15 and I17 are the scores for the questions 2, 4, 7, 9, 11, 12, 13, 15, and 17, respectively, as scored in (B) to determine an A score, and wherein an A score of 15 or more indicates severe deactivation, an A score of between 10 to 14 indicates moderate deactivation, an A score of between 5 to 9 indicates mild deactivation, and an A score of 4 or less indicates no significant deactivation;

(iii) further using the patient's M score for demodulation and the patient's A score for deactivation to select at least one medication appropriate for the patient which affects the demodulation and/or deactivation using the following criteria:

wherein the M score is greater than 4, the patient is classified as demodulated and is indicated to receive treatment with at least one serotonergic antidepressant medication;

wherein the A score is greater than 4, the patient is classified as deactivated and is indicated to receive treatment with at least one catecholaminergic antidepressant medication;

wherein both the M and the A score are each greater than 4, the patient is classified as mixed and is indicated to receive treatment with either (i) at least one serotonergic antidepressant medication and at least one catecholaminergic antidepressant medication or (ii) at least one dual mechanism antidepressant medication; and (iv) wherein when the patient is classified as demodulated, the patient is additionally administered an appropriate dosage of the at least one serotonergic antidepressant medication; or wherein when the patient is classified as deactivated, the patient is additionally administered an appropriate dosage of the at least one catecholaminergic antidepressant medication; or wherein when the patient is classified as mixed, the patient is additionally administered an appropriate dosage of either (i) the at least one serotonergic antidepressant medication and the at least one catecholaminergic antidepressant medication, or (ii) the at least one dual mechanism antidepressant medication.

2. The method of claim 1, wherein the at least one serotonergic antidepressant medication is selected from the group consisting of citalopram, fluoxetine, fluvoxamine, paroxetine or sertraline.

3. The method of claim 1, wherein the at least one catecholaminergic antidepressant medication is selected from the group consisting of bupropion or bupropion SR.

4. The method of claim 1, wherein the at least one dual mechanism antidepressant medication is selected from the group consisting of venlafaxine and mirtazapine.

5. The method of claim 1, wherein the questionnaire is manually taken by the patient by paper and pencil and is scored by hand.

6. The method of claim 1, wherein the answers to the questions of the questionnaire are processed and scored by a computer, with the computer providing the recommended antidepressant therapy.

7. The method of claim 6, wherein the computer keeps track of the patient's prior scores to provide a record of the patient's history and to monitor the patient's response to the treatment.

8. The method of claim 1, wherein the method is further used to recommend dosing for the medications prescribed.

9. The method of claim 1, wherein the method is further used to determine the presence of a bipolar syndrome by determining the level of depression and/or mania and the contributing dimensions of modulation, activation, demodulation and/or deactivation in a patient utilizing a bivalent number scoring criteria, wherein said bivalent number scoring criteria is evaluated via elevated M and A scores that represent positive demodulation and/or deactivation levels, correlate to the degree of depression the patient is experiencing, wherein an A score ranging from −5 to −9 suggests the presence of hypomania in the patient and an A score ranging from −10 to −26 suggests the presence of mania in the patient.

10. The method of claim 1, wherein an M and/or A score in the range of −1 to −5 indicates that the patient is functioning at a better level of modulation and/or activation, respectively, than usual.

* * * * *

UNITED STATES PATENT AND TRADEMARK OFFICE
CERTIFICATE OF CORRECTION

| | |
|---|---|
| PATENT NO. | : 7,553,834 B2 |
| APPLICATION NO. | : 10/199529 |
| DATED | : June 30, 2009 |
| INVENTOR(S) | : Richard J. Metzner et al. |

It is certified that error appears in the above-identified patent and that said Letters Patent is hereby corrected as shown below:

In the Claims

Column 9, Claim 1, line 10          After "score"

Insert -- of --

Signed and Sealed this

Fifteenth Day of June, 2010

David J. Kappos
*Director of the United States Patent and Trademark Office*